United States Patent
Stahl

[11] Patent Number: 5,190,731
[45] Date of Patent: Mar. 2, 1993

[54] PROCESS AND APPARATUS FOR EXOTHERMIC REACTIONS

[75] Inventor: Henrik O. Stahl, Rungsted Kyst, Denmark

[73] Assignee: Haldor Topsoe A/S, Denmark

[21] Appl. No.: 743,393

[22] PCT Filed: Feb. 12, 1990

[86] PCT No.: PCT/DK90/00034
§ 371 Date: Aug. 15, 1991
§ 102(e) Date: Aug. 15, 1991

[87] PCT Pub. No.: WO90/09234
PCT Pub. Date: Aug. 23, 1990

[30] Foreign Application Priority Data
Feb. 16, 1989 [DK] Denmark .................. 713/89

[51] Int. Cl.$^5$ .................................. F28D 7/10
[52] U.S. Cl. ........................... 422/148; 422/197; 422/201; 422/211; 422/239
[58] Field of Search ............ 422/148, 211, 218, 239, 422/200, 201, 197

[56] References Cited
U.S. PATENT DOCUMENTS

| | | | |
|---|---|---|---|
| 1,741,309 | 12/1929 | Jaeger | 422/148 X |
| 1,953,938 | 4/1934 | Jaeger | 422/197 X |
| 2,639,224 | 5/1953 | McAfee | 422/218 |
| 3,459,511 | 8/1969 | Jotoku et al. | 422/148 |
| 4,321,234 | 3/1982 | Ohsaki et al. | |

OTHER PUBLICATIONS

C. van Heerden, Autothermic Processes, Properties and Reactor Design—Mar. 30, 1953.
J. J. Hay and I. M. Pallai, Calculation Problems of Ammonia Synthesis Converters—Mar. 16, 1962.

Primary Examiner—Robert J. Warden
Assistant Examiner—Amalia L. Santiago
Attorney, Agent, or Firm—Ostrolenk, Faber, Gerb & Soffen

[57] ABSTRACT

A cooled reactor for exothermic catalytic conversion of gaseous materials, e.g. for the oxo synthesis, for the conversion of hydrogen and nitrogen to form ammonia and for the reaction of carbon oxides with hydrogen to form methanol, comprises a cylindrical pressure shell (10), distributor means (34) for synthesis gas, at least one tube sheet (30) and one or more catalyst beds (20) provided with cooling tubes (38) for the indirect cooling of reacting gas. Each cooling tube (38) consists of an outer tube (4) provided with a heat exchanging outer wall (7); this outer tube surrounds and is coaxial with an inner tube (2) and hence defines an annular space the inner wall of which is provided with perforations (8) to direct the stream of cooling gas, which may consist of or contain components of the synthesis gas, to the annular space and along the heat exchanging wall. There is obtained a very rapid equalization of temperature differences in the catalyst bed, which causes an improved yield and hence makes it possible to decrease the amount of catalyst for a given process.

4 Claims, 4 Drawing Sheets

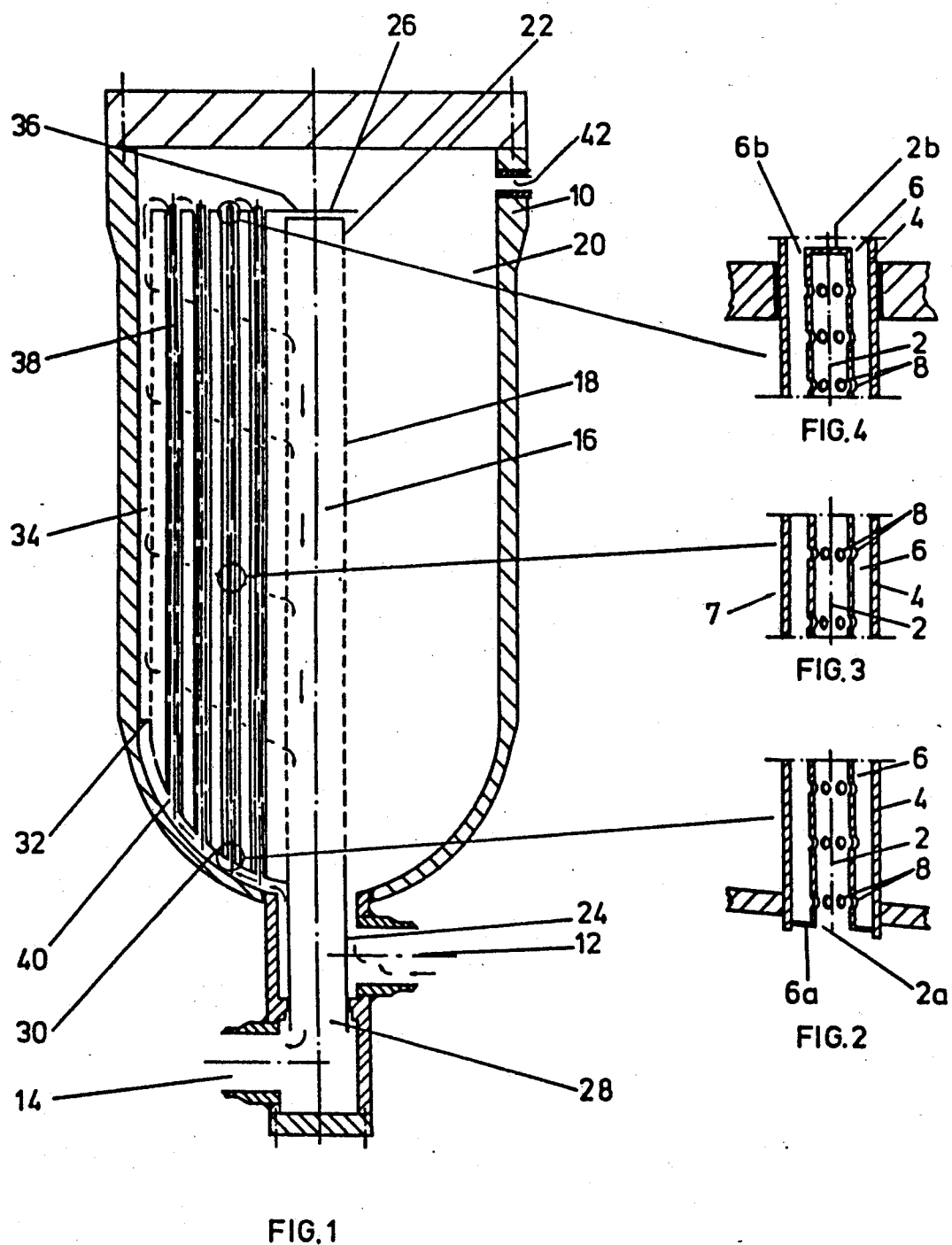

PROCESS AND APPARATUS FOR EXOTHERMIC REACTIONS

FIELD OF THE INVENTION

The present invention relates to a cooled reactor for carrying out catalytic reactions This reactor is of the kind comprising a cylindrical pressure shell, at least one tube sheet, means for passing the gaseous raw materials as a synthesis gas in a substantially radial direction through at least one catalyst bed provided with one or more cooling tubes for the indirect cooling of reacting gas, each cooling tube having a lower inlet end, an upper outlet end and an outer heat exchange wall.

The invention also relates to a process for carrying out exothermic reactions of gaseous raw materials in one or more catalyst beds in the reactor according to the invention.

BACKGROUND OF THE INVENTION

Exothermic reactions often take place in catalytic conversions accomplished by passing a process stream of gaseous raw material through a bed of a solid catalyst under convenient pressure and temperature conditions. The synthesis of ammonia or methanol and the Fischer-Tropsch synthesis are important industrial examples of this kind of processes.

The heat of reaction evolved in exothermic reactions increases the temperature of the process stream and the catalyst and this often results in deterioration of the catalyst performance and in reduction of the concentration of intended products because the overall reaction rate responds vigorously to changes of the temperature and distribution of the temperature in the catalyst layer or bed. In case of reversible exothermic reactions, the equilibrium concentration of the product is declining with increasing temperatures, thus getting more unfavourable at high temperatures.

The temperature profile in the catalyst layer during exothermic reactions depends not only on the rate of the evolution of heat of reaction but also on the method of removing heat from the catalyst bed to avoid excessive elevation of the temperature of the reacting gaseous material and the catalyst.

Substantially three different methods are used for removing the heat of reaction from the catalyst bed: direct cooling by mixing with a cold feed gas; indirect cooling by heat exchangers; and using cooling tubes in the catalyst bed.

A method which is frequently used at present for removing excessive heat is heat exchange between a high temperature gas leaving the catalyst layer and a cold feed (synthesis) gas, thereby elevating the temperature of the feed gas to a level necessary for initiating the reaction. Gas-gas heat exchanging units are thereby usually disposed centrally in or after one or more catalyst beds. However, in this manner only minor parts of the catalyst bed will be at optimum temperature; and consequently, by this method large parts of the catalyst bed suffer from insufficient temperature control.

To remove heat of reaction more uniformly from the entire catalyst bed, there has been designed reaction vessels in the prior art which are provided with cooling tubes which extend through different regions of the catalyst bed. Thereby excessive heat is transferred to a cold feed gas or to an external cooling medium. The gas or medium which enters the cooling tubes extending through the catalyst bed absorbs the heat evolved in the reaction. As the temperature of the reacting gas in the catalyst bed increases, the temperature difference between the reacting gas and the cooling tubes will increase and the temperature will thereby in some regions of the catalyst bed exceed the temperature for a maximum reaction rate. Therefore, the temperature control is sluggish and temperature oscillations around the cooling tubes dampen out very slowly. Reactors based on such a design are the known counter-current axial flow ammonia converter of the Tennessee Valley Authority type (TVA) as described in Industry. Engn. Chem. 45 (1953), 1242 and the co-current axial flow ammonia converter of the Nitrogen Engineering Corporation, mentioned in Br. Chem. Eng. 8 (1963), 171.

Cooling of a radial flow reactor constitutes a special problem: in order to carry out the cooling surface has to be kept constant throughout the height of the catalyst bed although it may vary with the radial position in the bed.

A method disclosed in U.S. patent application Ser. No. 4,321,234 for removing the heat of reaction in a radial flow reactor is to evaporate a liquid under a convenient pressure by passing a liquid cooling medium through cooling tubes. A cooling medium in the form of a rising stream is introduced and distributed via a system of distribution tubes into a number of second distribution tubes and then to a large number of cooling tubes connected to the second distribution tubes controlling the temperature inside the catalyst bed.

However, the large number of tubes connected to each other and the necessary piping results in a complicated network construction which renders the filling or refilling of catalyst charges a troublesome operation. A serious disadvantage of this method is even the risk of poisoning the catalyst by cooling media in case of leaks in the tube or piping system.

Another disadvantage of the method disclosed in the above U.S. Patent is the demand of external preheating of the feed gas to a temperature required for initiating the reaction in the catalyst bed and adjusting the boiling point of the cooling medium to a level which is just below or about the temperature inside the catalyst bed and which is determined by the kind of the conversion reaction.

DISCLOSURE OF THE INVENTION

It is, therefore, an object of the present invention to provide an apparatus wherein gaseous raw materials are reacted exothermically by passing a stream of the gaseous raw material in a radial direction through a catalyst bed under optimal temperature control achieved by cooling tubes preferably arranged in elongated cooling zones for a gaseous cooling medium disposed axially throughout the catalyst bed without the known complications.

According to the invention, each cooling tube consist of a fluid-tight heat exchanging outer tube coaxial with and surrounding an inner tube fitted in a fluid-tight manner to the inlet end of the cooling tube and thereby defining an annular space between the outer and inner tubes, the annular space being open at the outlet end of the cooling tubes, said inner tube being open at its inlet end and closed at the outlet end and being provided in its wall with a plurality of perorations throughout its length for directing a stream of cooing gas to the annular space and along the heat exchanging outer wall of the cooling tube.

It is hereby obtained that the gas streaming into the inner tube and along its entire length is distributed evenly in the annular space (and hence along the entire amount of catalyst in the bed in question), whereby the annular space is maintained at a constant temperature between the temperature of the surrounding catalyst and the outlet temperature of the gas.

In a preferred embodiment of the reactor according to the invention the temperature distribution in the catalyst bed is optimized by arranging the cooling tubes in a number of coaxial cooling zones containing staggered rows of cooling tubes, in order to obtain regions with adiabatic reaction and regions with cooling in the catalyst bed.

According to the invention the inner, perforated tubes of the cooling tubes may be slightly conical.

As mentioned the invention also relates to an improved process for exothermic reactions of gaseous raw materials in one or more catalyst beds in a reactor as described. According to the invention the gaseous raw materials are passed through at least one catalyst bed containing axially arranged cooling tubes, and passing a cooling gas through the perforated inner tubes of the cooling tubes to the annular space and along the heat exchanging outer wall of the outer tube of the cooling tubes in order to remove excessive heat of reaction from the catalyst bed by indirect heat exchange with the cooling gas.

In a preferred embodiment of the process according to the invention, the annular space inside the cooling tubes is kept at a constant temperature between the temperature of the surrounding catalyst and the temperature of the incoming synthesis gas by passing the gaseous raw materials in a substantially radial direction through the catalyst bed.

According to the invention the cooling gas may advantageously contain the gaseous raw materials (i.e. synthesis gas) which are preheated by indirect heat exchange with reacting gas in the catalyst bed to a temperature necessary for maintaining the conversion of the gaseous raw materials in the catalyst bed to a stream of product gas.

With the reactor and the process provided by the invention, the reaction yield is improved, which makes it possible to reduce the amount of the catalyst by about 20% compared to known radial flow reactors, thus saving necessary capital costs at a rate of about 25%.

BRIEF DESCRIPTION OF THE DRAWINGS

In the drawings,

FIG. 1 shows schematically a reactor of the invention in axial section,

FIG. 2, FIG. 3 and FIG. 4 in larger scale show axial sections of a bottom part, a central section and an upper part, respectively, of a cooling tube in a reactor according to the invention.

DETAILED DESCRIPTION OF THE INVENTION

Figure 5:
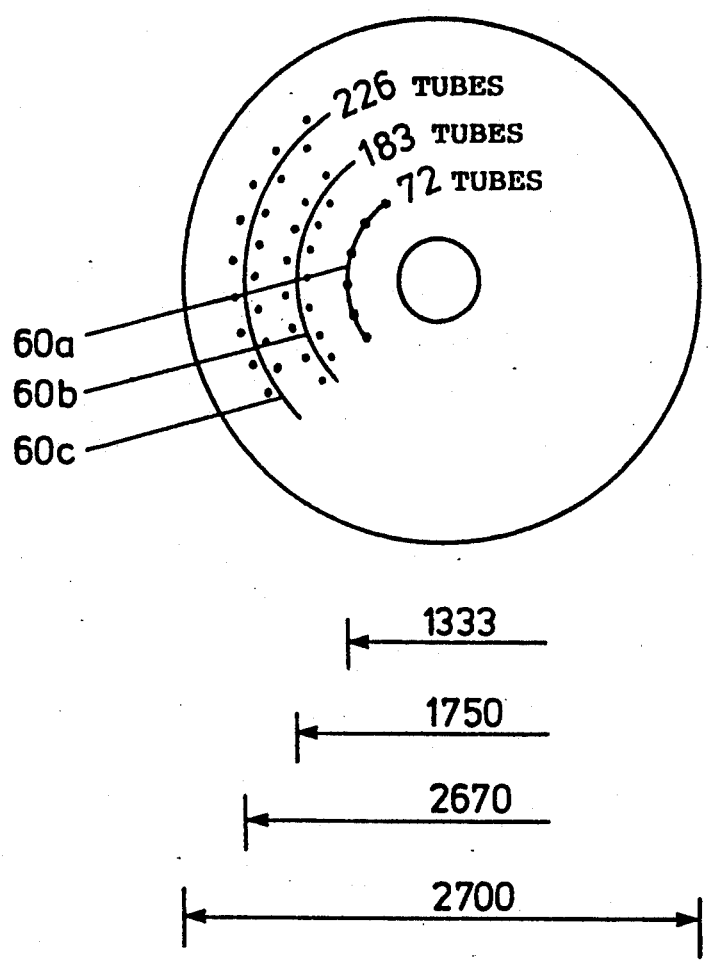
FIG. 5 is a schematical horizontal section of an embodiment of a reactor according to the invention with concentric cooling zones provided with cooling tubes in staggered rows.

The reactor shown schematically in FIG. 1 has a pressure shell 10 which constitutes the outer surface of the reactor. The reactor shell is provided with an inlet 12 for incoming gas and an outlet 14 for product gas. A central pipe 16 is connected to the outlet 14 in the conventional manner. The central pipe 16, which serves at receiving reacted gas (product gas) from a catalyst bed 20, has a perforated wall 18 extending through the catalyst bed 20 and a gas-tight wall 22 at its upper end, extending from the gastight end 26 into the upper part of the catalyst bed 20. The lower end of the central pipe 16 has a gastight wall 24 extending from the bottom of the catalyst bed 20 to the open end 28 of the central pipe 16 adjacent the outlet end 14.

Other essential parts of the reactor are a bottom tube sheet 30, a cover sheet 36, one or more gas distribution means 34 affixed to the circumferential part of the pressure shell 10 and cooling tubes 38 extending in an axial direction from bottom tube sheet 30 through catalyst bed 20 to cover sheet 36. A closable further inlet opening 42 for gas may be present near the top of the reactor.

As shown in FIGS. 2 to 4, each cooling tube 38 consist of two concentric tubes, an inner tube 2 and an outer tube 4, defining an annular space 6 between them. The inner tube 2 is open at the lower, inlet end 2a and closed at the upper, outlet end 2b and has a plurality of openings 8 distributed over its length for directing jets of incoming cooling gas into the annular space 6. The lower edge 6a of the inner tube 2 is bent towards the wall of the outer tube 4 and fitted to the bottom edge of the outer tube 4, thus providing a gastight lip 6a connecting the walls of the cooling tube 38. The outer tube 4 is fitted into the bottom tube sheet 30 and the cover sheet 36 whereby the annular space 6 is closed at its lower end 6a and open at its upper end 6b.

The cooling tubes 38, which optionally may be distributed uniformly in the catalyst bed, are arranged in the catalyst bed 20 in a number of cooling zones 60a, 60b, 60c... as schematically shown in FIG. 5.

The cooling zones 60a, 60b, 60c..., each containing a convenient number of cooling tubes 38, are distributed coaxially throughout the catalyst bed to obtain regions with adiabatic reaction and regions with cooling in the catalyst bed 20.

The operation of the reactor as described hereinbefore for producing ammonia will now be discussed in general with reference to FIGS. 1 to 5.

A stream of incoming gas, which is to serve as synthesis gas as well as cooling gas, is introduced via inlet 12 into a space 40 adjacent the lower part of the pressure shell 10 and confined by a cover plate 32 of the gas distribution unit 34 and the bottom tube sheet 30, which is fitted to the inner circumferential position of the pressure shell 10.

From space 40 the gas enters the lower end of the inner tube 2 of each of the cooling tubes 38. The gas is forced through the openings 8 along the entire wall of the inner tube 2 and is thereby distributed uniformly into the annular space 6 and along the heat exchanging wall 7 of the outer tube 4.

The slightly conical inner tube 2 is provided with the several openings 8 and supplies a uniform gas flow to the annular space 6 with constant velocity along the heat exchanging wall 7 of the outer tube 4. The gas leaves the annular space of the cooling tubes 38 at the upper end 6b and becomes effectively the reacting synthesis gas.

As by virtue of the gas distribution unit 34 the reacting gas has a substantially radial direction of flow, the temperature of the catalyst bed will be constant adjacent and along the entire outer heat exchanging wall 7 of the cooling tubes 38, which by constant heat transmission ensures a constant temperature inside the annular space 6

In case of the incoming cooling gas being a synthesis gas such as an ammonia synthesis gas, the gas is introduced into the gas distribution unit 34 after leaving the cooling tubes 38 and uniformly distributed to the catalyst bed 20. The reacting gas passes in radial direction and substantially at right angles to the cooling tubes from the gas distribution unit to the central pipe 16, thereby passing regions with adiabatic reaction and regions with cooling in the cooling zones 60a, 60b, 60c. ... The product stream of synthesis gas is passed from the central pipe 16 to the outlet 14.

The invention as described hereinbefore is generally applicable to catalytic reactions where gaseous raw materials are reacted exothermically to form gaseous products. Typical catalytic reactions to which the invention is applicable are the reaction between carbon oxides and hydrogen to methanol, oxosyntheses, and the catalytic conversion of hydrogen and nitrogen to ammonia.

In case of other syntheses than ammonia synthesis it may frequently be expedient either to admix the synthesis gas with smaller or larger amounts of inert gases; or to use a separate inert gas as the cooling gas and admit it through the inlet 12, and introduce the synthesis gas through the inlet opening 42 near the top of the reactor.

In the following examples the invention is applied in computation models illustrating various advantages of the reactor and process according to a preferred embodiment of the invention.

EXAMPLE 1

A modelling procedure is utilized for an ammonia plant simulated as a number of back-mix reactors in series with a production capacity of 1000 metric tons per day by using the process and the reactor of the invention as shown in FIGS. 1 to 5.

The catalyst used in the modelling procedure is the conventional ammonia catalyst KM 1.5-3 supplied by Haldor Topsoe A/S, Lyngby, Denmark, having a particle size of 1.5-3 mm and a density of 2700 kg/m$^3$. The catalyst bed 20 is set to a total volume of 46 m$^3$ and a height of 10 m.

The composition of the incoming gas, which functions both as cooling gas and synthesis gas, and the composition of the product stream and further data related to Example 1 are shown in Tables I to III hereinafter. The reactor is operated at a pressure of 140 kg/cm$^2$g. A process stream of synthesis gas of 500,000 Nm$^3$/h having an inlet temperature of 266° C. is introduced via the inlet 12 and the tube sheet 30 at the bottom of the reactor shell, which serves to distribute the incoming gas to the lower ends 2a of the inner tubes 2 of the cooling tubes 38. These are axially arranged as two staggered rows in each of three coaxial cooling zones 60a, 60b, 60c comprising 72 tubes, 183 tubes, and 226 tubes, respectively. Along the heat exchanging wall 7 of the cooling tubes the gas adopts a constant temperature between the temperature of the incoming gas and the temperature of the reacting gas.

After leaving the cooling tubes, the process stream of reacting gas is forced via the gas distribution unit 34 into a substantially radial direction through the catalyst bed 20.

Figure 6:
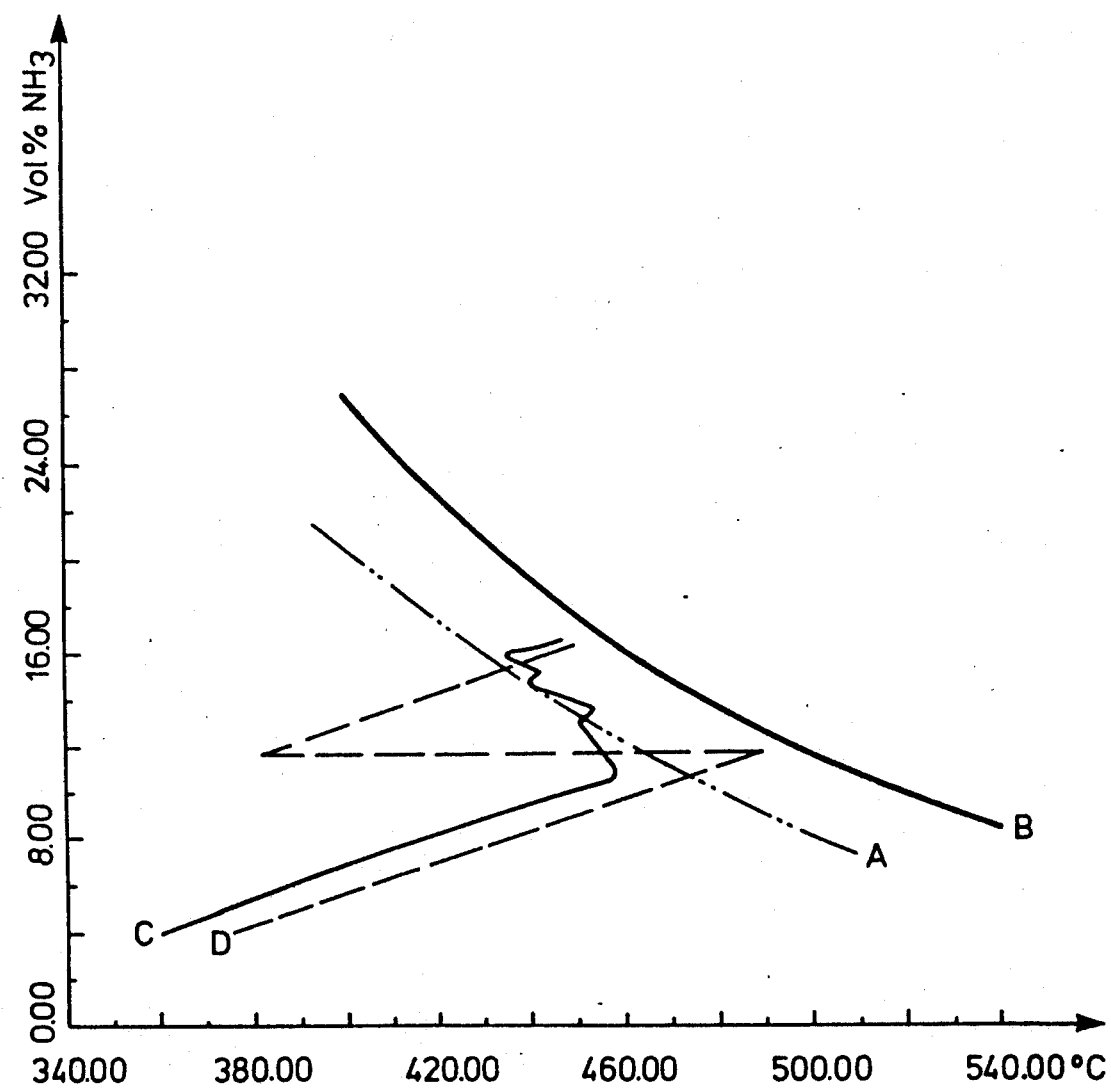
FIG. 6 and FIG. 7 show comparative plots of the concentration/temperature profiles in ammonia synthesis.
Figure 7:
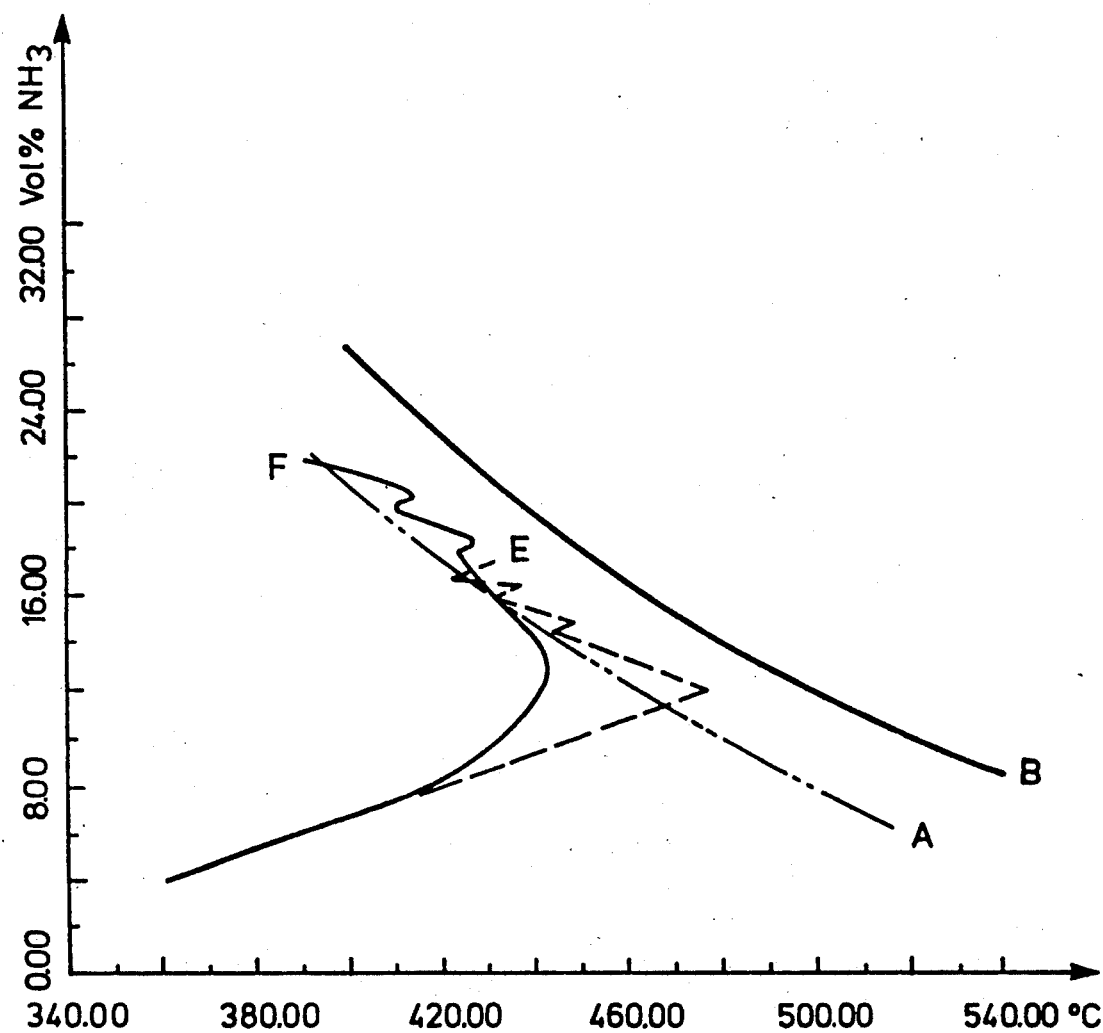

While passing through the catalyst bed, the temperature of the process stream increases in the adiabatic regions outside the cooling zones because of the exothermic reaction and decreases inside the cooling zones by indirect heat exchange with cold incoming gas in the cooling tubes. Thus only small temperature oscillations occur which dampen out very quickly as seen in FIGS. 6 and 7.

The ammonia concentration in the process stream is increased from 4.1 to 16.6 vol % by continuously passing the stream through adiabatic and cooling regions. The product stream formed from the synthesis gas is then received in the central pipe 16 and passed to the outlet 14 at a temperature of about 450° C.

EXAMPLE 2

The reactor and process of Example 2 are the same as described in Example 1 except for the following features:

The volume of the catalyst is raised from 46 to 56 m$^3$ and the flow of synthesis gas is decreased to 480,000 Nm$^3$/h.

The number of cooling tubes 38 in the first cooling zone 60c is increased from 226 as in Example 1 to 348, arranged in three staggered rows instead of two, and in the third cooling zone 60a from 72 to 125. The yield of ammonia is hereby improved from 16.6 to 17.4 vol % though the gas flow is reduced by 4%. The outcoming product gas has a temperature of 430° C.

Other parameters of the process and the reactor will be apparent from Tables I-III. The temperature-ammonia concentration profile of the process is shown in FIG. 7 as a dotted line.

EXAMPLE 3

The process and reactor of this Example is the same as described in the foregoing examples, except that there are now 894 cooling tubes distributed as two staggered rows and arranged in 5 cooling zones 60a-60e as further specified in Table III.

The catalyst volume is raised to 128 m$^3$ and the flow of synthesis gas is decreased to 380,000 Nm$^3$/h.

The amount of ammonia in the product gas is further improved to 21.8 vol %. The temperature of the outcoming product gas is 392° C.

Other process parameters will be apparent from Tables I-III.

COMPARATIVE EXAMPLES

FIG. 6 shows the concentration-temperature profile of the process according to Example 1 in comparison with the profile of a simulated process obtained in the known two-bed radial flow converter S-200 as described in U.S. patent application Ser. No. 4,181,701, equipped with a centrally mounted heat exchanger in the first catalyst bed.

In FIG. 6, curve B represents the thermodynamic equilibrium concentration at the conditions for the process and at the synthesis gas composition used in Example 1 (cf. Table I). Curve A illustrates an approach to this equilibrium by 10° C., which is a reasonable approach obtainable in practice.

Curves C and D represent changes occurring in the temperature and the ammonia concentration of the process stream of synthesis gas during its passage through the catalyst bed for the ammonia synthesis process.

The concentration-temperature profile for the process of Example 1 according to the invention is represented in FIG. 6 by the solid line C whereas the dotted line D represents the course of the process obtained in the S-200 converter. All the process parameters used in the S-200 reactor are equal to those described in Example 1, except the amount of catalyst, which is 56 m³ in the S-200 reactor instead of 46 m³ used in the reactor according to the invention.

Both reactors are simulated as a number of back-mix reactors connected in series. As seen from FIG. 6, replacement of the S-200 heat exchanger by cooling tubes mounted in several cooling zones compared with the known reactor causes a remarkable dampening of temperature oscillation around the optimum reaction-temperature curve A.

The amount of ammonia in the product stream is the same in both cases though the catalyst volume in the reactor of the present invention is reduced by nearly 20%.

The effect on the temperature-ammonia concentration profile caused by increasing the number of cooling tubes in the reactor according to the invention is further shown in FIG. 7, in which curves A and B are the same as in FIG. 6. Thus, a good approach to the optimum reaction curve A is represented by the dotted line E, which represents the process described in Example 2 (altogether 656 tubes). By mounting a still larger number (894) of cooling tubes inside the catalyst bed, as shown by the solid line F representing Example 3, the temperature differences between the adiabatic and cooling regions can be smoothed still closer in the region with maximum rate of reaction, compared with the process described in Example 1 (481 tubes).

TABLE I

| Parameters relating to the feed gas | |
|---|---|
| Example | 1 to 3 and comparative examples |
| Feed gas composition, vol % of incoming gas | |
| $H_2$ | 66.00% |
| $N_2$ | 22.00% |
| $NH_3$ | 4.12% |
| Ar | 2.50% |
| $CH_4$ | 5.38% |
| Pressure, kg/cm²g | 140 |
| Production Capacity of Reactor, metric tons/day | 1000 |
| Type factor | 1.7 |
| Catalyst density, kg/m³ | 2700 |
| Central Pipe, OD*, mm | 500 |

TABLE II

| Example | 1 | 2 | 3 | Ref. S-200 |
|---|---|---|---|---|
| Stream Rates, 1000 Nm³/h | 500 | 480 | 380 | 500 |
| Stream Temperature, °C. | | | | |
| Feed Stream at reactor inlet | 266° C. | 266° C. | 266° C. | 266° C. |
| Product Stream at reactor outlet | 448 | 430 | 392 | 448 |
| Product Stream Composition, vol % $NH_3$ | 16.6 | 17.4 | 21.8 | 16.6 |
| Catalyst Volume, m³ | 46 | 56 | 128 | 56 |
| Catalyst bed, | | | | |
| OD*, m | 2.7 | 3.0 | 3.0 | 3.0 |
| height, m | 10.0 | 10.0 | 25.0 | 10.0 |

*outer diameter

TABLE III

| Coefficients of heat transmission | |
|---|---|
| Cooling tube, OD, | 50 mm |
| Distance between tube axes | 60 mm |

| | Cooling zones | Diameter mm | Number of Tubes | Coefficient of heat transmission $h_y$ (kcal/m²h °C.) |
|---|---|---|---|---|
| Example 1 | 1 | 2166 | 226 | 274 |
| | 2 | 1750 | 183 | 314 |
| | 3 | 1333 | 72 | 373 |
| Example 2 | 1 | 2166 | 348 | 268 |
| | 2 | 1750 | 183 | 306 |
| | 3 | 1333 | 125 | 363 |
| Example 3 | 1 | 2583 | 270 | 121 |
| | 2 | 2166 | 226 | 134 |
| | 3 | 1750 | 183 | 152 |
| | 4 | 1333 | 125 | 178 |
| | 5 | 917 | 90 | 224 |

The coefficient of heat transmission $h_y$ at the outside of the cooling tubes is calculated according to standard formulas for crossflow inside a bundle of tubes when considering the reduced flow area caused by the catalyst particles.

INDUSTRIAL USE OF THE INVENTION

The invention is expected to be of great importance in the ammonia industry where the improved levelling out of the temperature difference in the catalyst bed will improve the yields of ammonia with a given amount of catalyst and hence reduce the costs. Similar results can be expected in other industrial exothermic reactions in which gaseous products are manufactured from gaseous synthesis gases, e.g. the Fischer-Tropsch synthesis and synthesis of methanol.

I claim:

1. A cooled reactor for carrying out exothermic catalytic reactions of gaseous raw materials, comprising:
    a cylindrical pressure shell containing at least one catalyst bed,
    at least one tube sheet located within the pressure shell,
    means for passing a synthesis gas in a substantially radial direction through said at least one catalyst bed,
    at least one cooling tube assembly supported by said at least one tube sheet, said at least one tube assembly for indirect cooling of reaction gas, each cooling tube assembly comprising a lower inlet end, an upper outlet end, an outer heat exchange tube and an inner tube, the outer tube being coaxial with and surrounding the inner tube, the inner tube being fitted to said at least one tube sheet in the inlet end of the cooling tube assembly, the inner and outer tubes defining an annular space located between the inner and outer tubes, the annular space being open at the outlet end of the cooling tubes, the inner tube being open at the inlet end and closed at the outlet end and being provided with a plurality of perforations for directing a stream of cooling gas into the annular space and along the outer heat exchange tube of the cooling tube assembly.

2. A cooled reactor as claimed in claim 1, wherein the reactor includes a plurality of cooling tube assemblies arranged in the reactor in concentric cooling zones containing staggered rows of the cooling tubes.

3. A process for the exothermic reaction of gaseous raw materials in a catalytic reactor having at least one catalyst bed, comprising the steps of providing a catalytic reactor having at least one catalyst bed and cooling tube assembly, passing gaseous raw materials in a substantially radial direction through at least one catalyst bed containing a cooling tube assembly and passing a cooling gas through a perforated inner tube of each cooling tube assembly to an annular space located within each cooling tube assembly and along a heat exchanging outer wall of an outer tube of each cooling tube assembly, to remove excessive heat of reaction from the at least one catalyst bed by indirect heat exchange with the cooling gas.

4. A process as claimed in claim 3, wherein the cooling gas comprises gaseous raw materials, the gaseous raw materials being preheated by indirect heat exchange with gas passing through the catalyst bed to a temperature for maintaining conversion of the gaseous raw materials inside the catalyst bed to a product gas.

* * * * *